United States Patent [19]
Lipson et al.

[11] Patent Number: 5,218,419
[45] Date of Patent: Jun. 8, 1993

[54] FIBEROPTIC INTERFEROMETRIC SENSOR

[75] Inventors: David Lipson, Indianapolis, Ind.; Nicolas Loebel, Seattle, Wash.

[73] Assignee: Eli Lilly and Company, Indianapolis, Ind.

[21] Appl. No.: 495,721

[22] Filed: Mar. 19, 1990

[51] Int. Cl.$^5$ .............................................. G01B 3/45
[52] U.S. Cl. ...................... 356/345; 250/227.19; 250/227.14
[58] Field of Search .................. 356/345; 250/227.14, 250/227.17, 227.19, 227.23, 227.27

[56] References Cited

U.S. PATENT DOCUMENTS

| | | |
|---|---|---|
| 4,577,551 | 12/1985 | Dyott . |
| 4,589,728 | 5/1986 | Dyott et al. . |
| 4,642,458 | 2/1987 | Jackson et al. ............ 250/227.17 X |
| 4,668,264 | 5/1987 | Dyott . |
| 4,669,814 | 6/1987 | Dyott . |
| 4,697,876 | 12/1987 | Dyott . |
| 4,712,866 | 12/1987 | Dyott . |
| 4,741,586 | 5/1988 | Kim et al. . |
| 4,753,497 | 6/1988 | Fujii et al. . |
| 4,784,454 | 11/1988 | Dyott . |
| 4,815,817 | 3/1989 | Levinson . |
| 4,866,660 | 9/1989 | Merkelo et al. . |
| 4,929,050 | 5/1990 | Wilson ............................ 356/345 |
| 4,974,961 | 12/1990 | Jackson et al. ..................... 356/345 |

OTHER PUBLICATIONS

Hocker, "Fiber-optic sensing of pressure and temperature", Applied Optics vol. 18, No. 9, pp. 1445-1448, May 1979.

Experimental Studies of Polymer Concentration Profiles at Solid-Liquid and Liquid-Gas Interfaces by Optical and X-Ray Evanescent Wave Techniques, F. Rondelez, D. Ausserre, and H. Hervet, Ann. Rev. Phys. Chem. 1987, 38:317-47.

Primary Examiner—Davis L. Willis
Assistant Examiner—Richard E. Kurtz
Attorney, Agent, or Firm—Robert E. Lee; Leroy Whitaker; Douglas J. Taylor

[57] ABSTRACT

An optical fiber interferometric system includes a pair of single-mode, polarization-preserving fibers having distal and proximal ends. The cladding of a selected portion of one of the fibers having been removed to allow an evanescent portion of a light wave traveling within the fiber to interact with any medium surrounding the selected portion of the fiber. A light source for producing a light of known character is coupled to the proximal ends of the pair of optical fibers for introducing a source signal to the pair of fibers. A reflector at the distal ends of the optical fibers reflects the light from the distal ends back toward the light source. The return signals are used to construct an interferogram which is observed to detect any modulation in the phase of the light signals. The modulation is examined ratiometrically to derive a change in the index of refraction of the medium surrounding the selected portion substantially free of any environmentally induced phase noise.

48 Claims, 3 Drawing Sheets

FIBEROPTIC INTERFEROMETRIC SENSOR

BACKGROUND OF THE INVENTION

The present invention relates to a fiberoptic sensor system for biomedical and other uses. More particularly, the present invention relates to a fiberoptic sensing system which utilizes a comparison of phase of one light beam relative to another, with one of the beams being sensitive to an analyte, and the other beam being used as a reference. The phase comparison is accomplished by an interference technique.

In conventional fiberoptic sensing systems, light at one or more wave lengths is transmitted from an optoelectronic base unit to a distal sensing element through a fiberoptic light guide. The distal sensing element is situated within an environment to be analyzed. The sensing element modulates incoming light in known proportion to the presence of one or more analytes that are situated within the environment. The modulated light is then returned to the base unit through the same input fiberoptic fiber, or through one or more alternative fibers. The level of the analyte or analytes may be inferred by quantitative assessment of the optical intensity returned from the sensor to the base unit with respect to the optical intensity transmitted to the sensor. Systems employing quantitative optical intensity assessment are herein referred to as intensity modulated sensing systems.

In one prior art intensity modulated sensing system, the sensing element consists of a reactive chemistry that is disposed substantially entirely within a hole formed inside a distal end of a multimode optical fiber itself. Light at one or more wavelengths is transmitted from the proximal end of the fiber to the perforated distal end where the light interacts with the reactive chemistry which can be composed of a fluorescent or optically attenuative material. The magnitude of the fluorescent emission, or the extent of the optical attenuation by the attenuative material, is generally proportional to the concentration of a particular analyte that is in contact with the distal end of the fiber. The fluorescent intensity, or the degree of optical attenuation, can be measured by instruments located at the proximal end of the fiber.

One problem associated with conventional intensity modulated sensing systems of this type is that the modulation of the light can be affected by factors other than the concentration of the analyte. If the multimode optical fiber is flexed during transduction, some of the light transmitted to the sensor may be lost by conversion of guided modes within the fiber to radiation modes. Additionally, some of the light returning from the sensor may be lost by the same mechanism. This loss of light may be incorrectly interpreted as a change in analyte concentration because a correlation is being made between the level of the analyte and the degree of light modulation. In fact, all factors affecting the absolute magnitude of the optical energy travelling within the fiber may be incorrectly interpreted by the system as changes in analyte concentration. These factors include, but are not limited to, variations in illumination intensity, changes in transmission at fiber connection points, and intrinsic changes within the sensor such as optical bleaching of the illuminated material.

Another problem associated with some intensity modulated sensing systems is the very low overall operating efficiency, often less than $10^{-10}$. This extremely low operating efficiency puts severe constraints on the systems. In order to maintain an adequate signal-to-noise ratio under these adverse conditions, high intensity illumination (e.g. laser or arc lamp) and high efficiency detectors (e.g. photomultiplier tubes) must be used. Complex and expensive wavelength selection devices are often required in order to optimally match the illumination to the sensing material. Because of the spectral energy and efficiency characteristics required of source and detector, attempts to convert conventional intensity modulated sensing system components to solid state optical devices have not been particularly successful in the biomedical sensing arena.

Some of the problems associated with some intensity modulated sensing systems can be overcome by employing a single-mode polarization-preserving fiberoptic waveguide to form an interferometric sensor system such as is shown in U.S. Pat. No. 4,697,876. In such a system, light from a coherent source such as a laser is directed through a beam splitter which sends half of the light into a reference fiber and the other half into a sensor fiber. The sensor fiber is coupled to the environment sought to be measured so that the phase of the light is modulated by an environmental signal. The light in both fibers is then recombined by a second beam splitter and fed to a photodetector responsive only to the amplitude of the combined signal. The system is adjusted to generate a sharp null with any change in environmental condition being reflected in a non-null signal. While such a system enjoys significantly enhanced sensitivity to environmental signals over intensity modulated sensing systems, the system as a whole exhibits other problems due to the Mach-Zehnder configuration of the system such as the need for optical detectors situated at the distal ends of the fibers, and the need for very complex signal processing algorithms to provide the desired quantification of the non-null signals.

It is therefore one object of the present invention to provide a fiberoptic sensing system which does not rely on intensity modulation to determine the concentration of one or more analytes.

Another object of the present invention is to provide a fiberoptic sensing system which is insensitive to environmental and other noise sources.

Yet another object of the present invention is to provide a fiberoptic sensing system that has an efficiency level substantially greater than conventional fiberoptic sensing systems.

Still another object of the present invention is to provide a fiberoptic sensing system that employs very simple signal processing algorithms to quantify the measured changes.

SUMMARY OF THE INVENTION

According to the present invention, an apparatus is provided for detecting a change in concentration of one or more species or analytes in a fluid medium. The apparatus includes a first and second singlemode optical fiber, with at least the first optical fiber having a sensing portion allowing a phase modulation of a guided light wave travelling within the fiber by the medium surrounding the sensing portion via the evanescent component of the wave. The apparatus also includes means for introducing a light of known character into both the first and second optical fibers. Additionally, means for optically mixing light emitted from the first and second optical fibers is provided so as to develop a fringe pattern which is characteristic of the mutual phase between the light in the two optical fibers. Means for observing the fringe pattern are provided so that reproducible characteristic changes in the pattern may be related to changes in analyte concentration. While the focus of the present invention is principally on in vivo detection and measurement of the concentration of one or more species or analytes, the apparatus can also be used to detect physical effects such as pressure, temperature, and strain, and the intended use of the apparatus should not be viewed as a limitation on the scope of the present invention.

Unlike conventional intensity modulated sensing systems, a fiberoptic sensing system of the present invention does not rely upon amplitude modulation of the light wave in the optical fiber, whether by an analyte or by any intermediate reactive chemistry. Instead, the present invention measures the analyte concentration by comparing the phase of two well-characterized light beams relative to each other. The optical fiber carrying one of the light beams is sensitive to the analyte as well as to noise sources, while the optical fiber carrying the other light beam is sensitive only to the noise sources. The level of the analyte can be inferred by optically superposing the two light beams to derive an interference pattern dependent only on analyte concentration. The noise contribution appears as a common mode signal in both light beams and does not affect the interference pattern.

The phase comparison is accomplished by directing the interference pattern onto a detector, or array of detectors, and the relative spatial position of the fringes correlated to the phase between the mixed beams, with the phase providing an indication of the analyte level. By phase-modulating the guided wave through interaction with the evanescent component of the wave, optical attenuation may be reduced to arbitrarily low levels. By utilizing phase rather than intensity measurement, the measurement of analyte level is rendered insensitive to energy loss due to fiber bending and other intensity modulating effects.

The overall efficiency of the system according to the present invention is sufficiently high to permit inexpensive and reliable solid state components to be used throughout. The interference method provides sensitivity at levels approaching the limits of known technology. This eliminates the need for high power illumination of the sensor. The measurement method is wavelength insensitive, at least to first order, so long as the wavelength selected is not close to an absorption peak of the analyte, thus allowing infrared laser diodes to be utilized as sources and germanium- or silicon-based photo sensors to be utilized as detectors. Because these types of solid state components are widely used in various industries including the telecommunications industry, the low cost and ready availability of these elements makes them highly desirable for use in systems of the present invention.

In interferometers such as are used in the present invention, the phase of the light beam in the sensing fiber will be changed whenever the optical path length of that fiber is changed. It will be understood that optical path length is the product of refractive index and physical path length. A change in either refractive index or physical path length creates a change in the optical path length. An interferometric sensor must therefore be capable of optical path length modulation as a function of analyte level. This optical path length modulation can be accomplished by a sensor which is sensitive to physical extension of one of the fiber arms to change the physical path length. Generally, such physical extension is achieved by changes in pressure, temperature, etc. The preferred sensor, however, is one in which the change in optical path length is due to a change in refractive index of an external medium.

One feature of systems of the present invention is that the first optical fiber includes a sensing portion which allows an evanescent portion of the guided wave travelling within the first fiber to interact with any medium surrounding this sensing portion. The evanescent component of the light wave will experience a velocity change with any change in the index of refraction of the medium surrounding the sensing portion. This velocity change is necessarily expressed as a change of phase of the guided light wave as a whole, relative to the undisturbed beam travelling in the second fiber. Since changes in analyte concentration are normally accompanied by refractive index changes over some linear range, the system is therefore rendered sensitive to the level of analyte present in the surrounding medium.

One advantage of this feature is that, by exposing only the evanescent portion of the guided light wave to the surrounding medium, the light beam remains trapped within the confined core geometry of the fiber and does not tend to spread into the medium as is the case with conventional end-fire geometries.

Another advantage of this feature is that the limited penetration depth of the evanescent wave into the surrounding medium reduces the optical attenuation which is associated with the passage of light through any medium, thus permitting a lower-power initial illumination.

Yet another advantage of this feature is that the decreased energy flux and shallow penetration depth cause less optically-induced degradation of the surrounding medium, an effect commonly ascribed to the formation of free-radicals during the process of fluorescence and commonly called photobleaching. The reduction of this photobleaching coefficient allows the use of low-concentration indicator species and extends useful lifetime of the sensor chemistry.

A major advantage of the invention is that analyte chemistries exhibiting absorbance changes rather than fluorescence changes can also be used, since absorbance changes cause changes in refractive index. Absorbant chemistries are much more prevalent than are fluorescent chemistries and are thus more easily incorporated into system designs. Further, at wavelengths associated with absorbance peaks in the spectrum, the refractive index can change violently with small changes in chemistry in the anomalous dispersion region.

Another feature of systems of the present invention is that means is provided for introducing light of known character into both singlemode fibers, principally by deriving each beam from the same coherent source, e.g. a laser. One advantage of this feature is that any change in phase cannot be due to a fluctuation of the light sources and must be due to a change in the medium surrounding the sensing portion which can be related to a change in analyte concentration.

In preferred embodiments of the present invention, at least a first optical fiber contains an elliptical core and a rotationally asymmetric cladding. One feature of the foregoing structure is that, by providing an elliptical core, polarization of the guided wave within the fiber is preserved. An additional feature of the foregoing structure is that by providing a rotationally asymmetric cladding, the cladding can be gradually removed in a symmetric manner which will expose one side of the core while still maintaining a portion of the cladding around the remainder of the core to retain the necessary structural integrity of the fiber.

Also according to the present invention, a method of detecting a change in concentration of an analyte in a fluid medium is provided. The method includes the steps of:

submerging a portion of an optical fiber in a fluid medium;

introducing a light of known character into the optical fiber; and observing the phase of the light in the optical fiber so as to detect a change in phase due to a change in analyte concentration in a fluid medium.

Thus, the present invention provides an apparatus and method for determining the concentration of an analyte by utilizing a fiberoptic sensing system which relies upon phase comparison to determine the concentration of the analyte. The system utilizes the evanescent wave portion of the guided wave to permit the guided wave to be sensitive to refractive index changes in the external medium. The evanescent wave thus interacts with the medium to produce a guided wave phase difference which is analyzed to determine the analyte concentration.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 5b is a perspective view of an etching technique which can be used to modify the optical fiber shown in FIG. 5a.

DETAILED DESCRIPTION OF THE DRAWINGS

Figure 1:
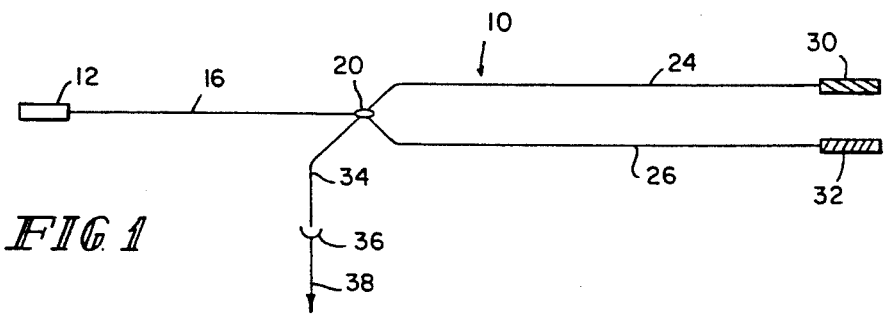
FIG. 1 is a diagrammatic view of a fiberoptic interferometric sensor according to the present invention.

FIG. 1 illustrates diagrammatically a basic fiberoptic interferometric sensor system 10 in accordance with the present invention. The system 10 is based upon the principles of a Michelson-type interferometer. The system 10 includes a laser diode source 12 which, in the preferred embodiment, can be a solid state infrared laser diode. Such infrared laser diodes are commonly available in the telecommunications industry, and several are adaptable for use with the present system 10. Such infrared laser diodes generally exhibit a high efficiency, low power requirement, long life, some wavelength tunability, optical coherence, intrinsic polarization, high brightness, compact footprint, and low cost.

A single-mode optical fiber 16 is provided which receives the output of the laser diode source 12. This source optical fiber 16 is connected to a commercially available fiberoptic coupler 20 which, as will be understood by those skilled in the art, distributes the input beam into two or more output fibers. The coupler 20 preserves the phase and frequency information of the input beam, but at reduced amplitude because the input light is split between each of the output fibers. In the illustrative embodiment, there are two output fibers 24 and 26. Specifically, fiber 24 is referred to as a sensing fiber and fiber 26 is referred to as a reference fiber. Both fibers 24 and 26 are single-mode optic fibers similar, although not necessarily identical in construction, to the first optic fiber 16. Additionally, all of the fibers 16, 24, and 26 are preferably polarization preserving fibers, that is, fibers in which the polarization of the laser beam is preserved. One particular configuration for the fibers 16, 24, and 26 to achieve this polarization preserving characteristic will be discussed below in relation to FIG. 5a.

The sensing fiber 24 has a sensor element 30 situated at its distal end. In the broadest sense, the sensor element 30 can be some type of sensing medium which is positioned adjacent the distal end of the sensing fiber 24, and which reacts with an analyte in a known manner to effect a refractive index change in the sensing medium. Alternatively, the sensor element 30 can be an adjacent volume of a fluid having a refractive index which will change in a known manner as the concentration of the analyte changes. In either case, this refractive index change in the sensing medium or sensor element 30 can be detected by exposing the evanescent portion of the light beam to the sensing medium. The use of only the evanescent portion of the wave and its characteristics will be discussed below in the discussion related to FIGS. 2 and 3.

The reference fiber 26 has a reference element 32 situated at its distal end. Both the reference fiber 26 and the sensing fiber 24 generally terminate with end face reflectors (not shown) which reverse the direction of the beam carried within each fiber, and redirect the beams back toward the coupler 20. At coupler 20 the two returning beams are mixed, or more correctly superposed with respect to each other, so that a comparison of phase can be made. The phase relation is characterized by an interference field generated by the autocorrelation of the two returning beams. Since the two returning beams are confined in single mode fibers, there is no relative tilt between the two beams, and the interference field generated exhibits a "recombinant spot" rather than "parallel fringe" appearance.

A detector unit 36 is provided which is attached to an output of the coupler 20 by optical fiber 34 which need not be polarization preserving. The optical fiber 34 and detector unit 36 receive the recombined wave generated by the superposing of the sensing and reference beams at the coupler 20. The amplitude of the superposed wave detected by the detector unit 36 at any instant in time represents the relative phase between the sensing and reference beams, for a given polarization angle of each beam. If the optical pathlength travelled by one of the beams is smoothly altered by one-half wavelength, the relative phase between the two beams will move from 0 to $2\pi$ radians in a sinusoidal fashion. This will cause a change in amplitude of the superposed wave detected by the detector unit 36 analogous to that which would be detected by orthogonally traversing the sinusoidal fringe field observed in tilted-wave interferograms. The half-wavelength repeat period is due to the double-pass nature of Michelson interferometers.

For completely coherent sensing and reference beams of equal power at identical polarization angles, "perfectly" destructive and constructive interference would occur with the resultant intensity of the superposed wave moving between zero and the input intensity of the source as a function of the phase. Conventionally a visibility coefficient is used as a measure of the superposition efficiency or "perfectness". The visibility coefficient is unity for perfect constructive and destructive interference and reduces towards zero as the efficiency decreases. Any decrease in superposition efficiency is generally attributable to non-aligned polarization angles, unequal power, or coherence imbalance between the two beams.

The output beam carried on fiber 34 representing the optical superposition of the sensing and reference beams impinges upon detector 36 which develops an output electrical signal 38 proportional to the incoming optical intensity of the superposed beam at the detector. A change in the optical path length of one of the beams results in a change in the output 38 of the detector unit 36 which is also a signal of sinusoidally varying value reflecting the half-wavelength phase relation of the interferometer. As indicated previously, a change in optical path length is experienced by the sensing beam as a result of any change in the index of refraction of the sensing element 30. Thus, the change in refractive index, and consequently a measurement of the level or presence of an analyte can be obtained from the signal output 38.

The Michelson interferometer design illustrated in FIG. 1 has advantages over other types of interferometers. First, having end face reflectors which reverse the direction of beam propagation and redirect it back towards the source permits the fiber ends to be situated in an analyte pool while the optoelectronic base unit (for example the laser diode 12 and detector 36) may be located at a remote site. This is in contrast to a Mach-Zehnder configuration, where the optical detectors must be situated at the distal ends of the fibers. Second, because the light traverses the same length of fiber twice in the Michelson-type interferometer, the optical pathway is made twice as sensitive to perturbations as compared to the single-path design of the Mach-Zehnder interferometer. Third, the entire length of fiber between the coupler 20 and sensor element 30 or reference element 32, respectively, is or can be made interferometrically sensitive, allowing coiled-coil sensor designs exhibiting improved sensitivity compared to short Fabry-Perot multiple-pass cavities of alternative design. Fourth, the interference pattern generated by a Michelson configuration is a well-characterized sinusoid. Other types of interferometer configurations result in more complex patterns which require more complex signal processing algorithms to be utilized to provide the desired measurement.

As indicated previously, it is possible to construct a sensor for use in the present invention in which a change in optical path length is achieved by a change in physical path length. For example, if an enzyme is attached to the fiber in one arm of a fiberoptic interferometer and the enzyme is permitted to convert substrate into product, the generally exothermic reaction will cause an elevation in local temperature. This temperature increase will cause the optical fiber to expand and thereby effect a physical path length change. This occurs for example with the oxidation of free glucose to hydrogen peroxide and gluconic acid in the presence of glucose oxidase attached to the fiber. However, as can be understood from the previous discussion, an interferometric sensor which relies solely on physical path length change is limited to detecting changes in physical properties such as pressure, temperature, and bending or tensile stress. A sensor based upon refractive index modulation is not limited to strictly physical property changes in the surrounding environment, but can also be applied to measurement of the concentration of a chemical species or analyte. Thus, any change in analyte level which results in a change in the refractive index of a sensing medium can be measured.

A particularly advantageous design is an interferometric sensor based upon refractive index modulation utilizing the evanescent portion of the guided light wave. It is known that the evanescent portion of a singlemode guided wave consists of a traveling wave extending beyond the core/cladding boundary into the less dense medium propagating as a traveling wave in the longitudinal direction of the optical fiber. The evanescent portion has a Bessel-K or Mathieu function electric field amplitude asymptotically approaching zero within one or two wavelengths in the transverse direction. This is in contrast to the discretized evanescent fields associated with step-index multimode waveguides of the prior art where the evanescent intensity drops exponentially into the less dense medium at each cladding reflection and, except for the small, finite, Goos-Hanchen shift, does not propagate as a traveling wave in the longitudinal direction.

Figure 2:
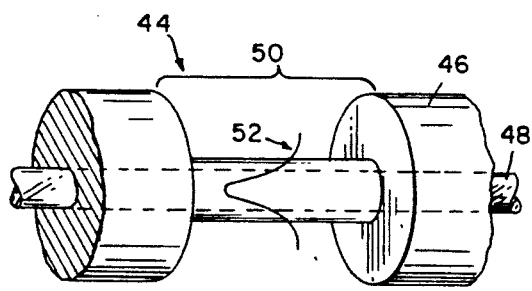
FIG. 2 is a much enlarged view of an etched optical fiber with a light wave diagrammatically shown in relation thereto.

Access to the evanescent wave can be accomplished without entry into the core of the optical fiber. FIG. 2 illustrates a section of a singlemode optic fiber 44 which includes a outer cladding 46 and an inner core 48. An etched area 50 is illustrated where a majority of the cladding 46 has been etched away to leave only a small layer of cladding surrounding the core 48. A single wavefront 52 of a light wave is shown schematically to illustrate the distribution across the diameter of the fiber of the optical energy being transmitted by the fiber 44.

Figure 3:
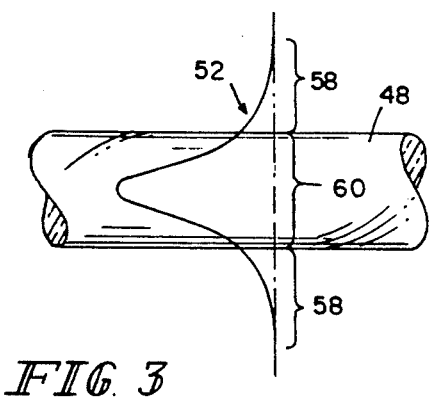
FIG. 3 is a detailed view of the etched portion of the fiber shown in FIG. 2.

FIG. 3 illustrates in greater detail a portion of the etched area 50 that is shown in FIG. 2. Specifically, FIG. 3 illustrates schematically the distribution of the optical energy within the light wave 52. The portion of the energy outside of the core 48 is defined as the evanescent field, and is identified by the number 58. The guided field 60 is the portion of the light wave contained within the core 48. It is generally understood that about 30% of a optical energy flowing in a singlemode optical fiber is present in the evanescent field 58 while about 70% of the optical energy is contained in the guided field 60, dependent upon development of a stable guided mode, fiber numerical aperture, cutoff wavelength, and V-parameter. The evanescent field penetration depth can be controlled by a number of factors including wavelength, external refractive index, selective reflectance coatings, source power, etc.

As can be seen in FIGS. 2 and 3, to have access to the evanescent wave portion of the light wave within the fiber 44, the fiber 44 must be etched to either expose the core itself, or etched to a point where the majority of the cladding has been removed such that the evanescent wave extends through the remaining cladding and is therefore accessible. With access to the evanescent portion 58, refractive index changes in the surrounding medium can affect the evanescent wave portion 58 of the light wave 52. With a refractive index change in the surrounding medium thus resulting in an optical path length change for the evanescent portion of the wave, the entire light wave 52 within the fiber 44 is affected thus creating a phase difference which can be measured by the system 10 illustrated in FIG. 1. Since refractive index has an intrinsic effect on optical path length, it is more sensitive and hence more reliably measurable by the system 10 than indirect or extrinsic effects such as the thermal expansion discussed earlier in connection with the glucose oxidase sensor.

Figure 4:
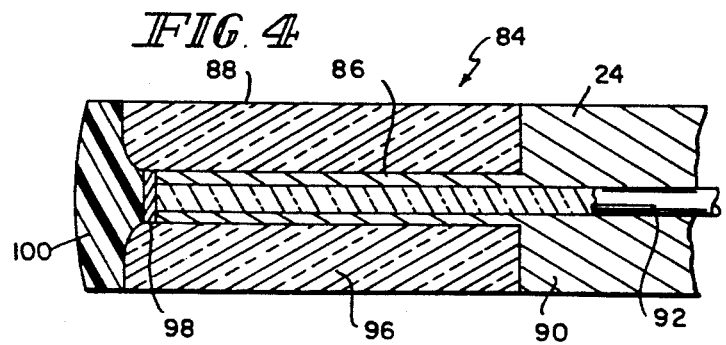
FIG. 4 is a sectional view of one embodiment for a sensor for use in the present invention.

FIG. 4 illustrates a typical intrinsic sensor configuration which can be utilized in the system 10 illustrated in FIG. 1. Specifically, FIG. 4 illustrates a pressure sensor 84 which, it will be understood, represents the sensor element 30 of FIG. 1. The pressure sensor 84 includes a sensing element 88 which is attached to an end portion 86 of the fiber 24. As can be seen in FIG. 4, a major portion of the cladding 90 around the end portion 86 of the fiber has been removed by etching or other means, and the sensing element 88 has been placed in the area where the cladding 90 has been removed. It will be understood that a sufficient portion of the cladding 90 has been removed to expose the evanescent wave component of the guided wave carried by the fiber 24. In the illustrative embodiment, a photoelastic element 96 has been placed around the etched area to form the sensing element 88. A reflector 98 is positioned at the end of the core 92 to reflect the light beam back toward the coupler 20. A filler end 100 is provided to provide structural integrity to the pressure sensor 84, protect reflector 98, and provide a smoothly varying cross-section for optimization of hemodynamic flow parameters.

Illustratively, the photoelastic element 96, composed for example of a material such as gallium phosphide (GaP), undergoes a propagation constant change upon exposure to pressure. The evanescent portion of the wave carried by the fiber 24 penetrates into the photoelastic element 96 where it is subject to the intrinsic propagation constant of the material. In the absence of an applied pressure, the effective refractive index of the sensor portion 30 is determined by the integrated contributions of core index 92, residual cladding index 90 and surrounding photoelastic element index 96. The sensing wave travelling in fiber 24 therefore assumes a stationary phase relative to the reference wave travelling in fiber 26. Upon application of a pressure to the sensor, the photoelastic constant of the sensing material is modulated by an amount proportional to the magnitude and direction of the applied pressure. The integrated refractive index through which the sensing wave passes is therefore altered, producing a corresponding change in the relative phase between the sensing and reference waves. The change in phase relationship may be detected at unit 36 after mixing of the two waves at coupler 20 as discussed previously, and the change in phase correlated to the applied pressure.

The element 96 can also be selected to be gas permeable to one or more gases of interest such as carbon dioxide. In a polymer such as polyacrylamide, the bulk refractive index may become a function of gas concentration or partial pressure. Ion-permeable membranes or membranes semi-permeable to selected species may be added to sensing element 96. Completely impermeable coatings, e.g. metals, are preferred in the case of a temperature sensor, where element 96 would consist of a compound selected for high refractive-index variation with applied temperature. Specifically, the element could consist of one or more organic solvents such a dichloromethane, trichloroethylene, or tetrahydrofuran, which all possess reasonably high refractive index/temperature coefficients.

Various other chemical and biochemical reactions are known which cause a change in the bulk refractive index of materials which can be used in the present invention. In general, the wavelength of the light used in connection with any such sensor can be selected to lie in the normal or anomalous dispersion spectral regions, but should not be exactly matched to absorbance peaks since the anomalous dispersion coefficient undergoes little change with absorption coefficient at this wavelength. The preferable operating wavelength is located at the maximum rate of change of chemical absorbance with wavelength, which generally occurs between about 1 and 25 nanometers to either side of a spectral absorbance peak.

One problem associated with etching a fiber as illustrated in FIGS. 2-4, is that when the cladding 46 is etched away to reveal the core 48, the fiber loses substantially all of its strength, and is easily breakable. It will be understood that the core 48 is extremely small in diameter, and has almost no strength when unsupported. Thus, etching as illustrated in FIG. 2 is generally undesirable, particularly where the etched fiber 44 will be used within a human body to measure the level of a body fluid component, etc. One way of obtaining access to the evanescent portion of the wave travelling within a fiber is to start with a D-shaped fiber as illustrated in FIG. 5a.

Figure 5A:
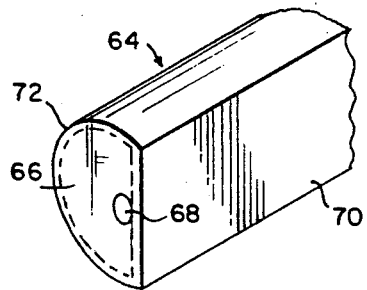
FIG. 5a is a perspective view of an optical fiber preferred for use in the present invention with the thick polymeric buffer or protective coat not shown.

Specifically, FIG. 5a illustrates a D-shaped fiber 64 which includes a cladding layer 66, and an elliptically shaped core 68. The fiber 64 has a flat side 70 which is closer to the core 68 than the opposite curved side 72. Because less cladding material 66 is present between the core 68 and the flat side 70, etching of the fiber 64 in an etching bath, such as a hydrofluoric acid etching bath, results in an asymmetrical exposure of the core. The flat portion 70 etches down to the core 68, so as to permit exposing a portion of the evanescent portion of the guided wave, while the remainder of the fiber is not significantly weakened in this etching process. A D-shaped fiber is available from Andrew Corporation, Orland Park, Ill., which is suitable for this application.

Figure 5B:
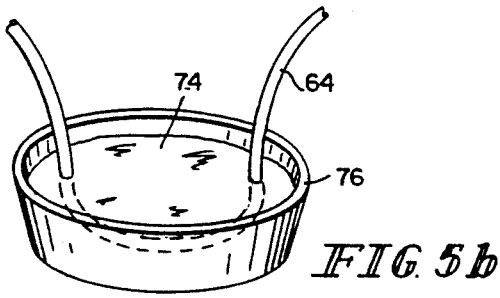

FIG. 5b illustrates the etching process, and specifically illustrates an etching solution 74 contained in a non-ceramic container 76. Illustratively, the etching solution 74 is a 10%–40% hydrofluoric acid solution. To perform the etching, a section of the D-shaped fiber 64 is immersed in the etching solution 74 for a period of time which can be between about 5 and 45 minutes, depending on acid concentration, temperature, etc. This period of time is dictated by the time necessary to etch the cladding 66 away from the flat side 70 of the fiber 64 until a sufficient portion of the core 68 is exposed, or at least until the cladding 66 is removed until the desired evanescent portion of the guided wave can be accessed.

One method of determining the proper amount of time for keeping the fiber 64 in the etching solution 74 is to use the interferometric sensor system 10 illustrated in FIG. 1 as previously described. Thus, if the fiber 64 to be etched is utilized as the sensing fiber 24 of FIG. 1, before the evanescent wave is exposed, the light beams in both of the fibers 24 and 26 will be at a fixed phase relationship. As soon as the evanescent wave portion is exposed by the etching process, the phase relationship will change. This change in phase relationship will be caused by the evanescent wave portion being exposed to, and being affected by, a refractive index change created by the etching solution 74. Thus, as soon as the change in phase relationship is identified, one can remove the fiber 64 from the etching solution 74 and stop the etching process by immersion into a dilute alkali such as aqueous sodium bicarbonate followed by distilled water. The etching process can be taken to any arbitrary depth in this manner, ensuring that the requisite portion of the evanescent wave has been exposed.

Figure 5C:
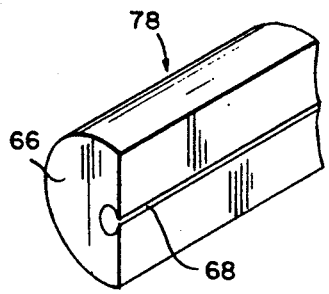
FIG. 5c is a perspective view of the fiber shown in FIG. 5a following an etching process.

FIG. 5c illustrates an etched fiber 78 which has been etched according to the procedure described above. Although FIG. 5c illustrates that the core 68 has been exposed, it will be understood that a small portion of the cladding 66 can remain over the core 68 and still have the evanescent wave portion accessible. A sensor of a type previously discussed in connection with FIG. 4 can be added to the etched D-shaped fiber. Alternatively, after addition of a reflector 98, the etched D-shaped fiber can be merely immersed in an environment of interest which is expected to undergo changes in bulk index of refraction with the result that the changes can be directly detected by the exposed evanescent portion of the guided wave.

Although the embodiments described above relate to a workable sensor system which can be utilized to measure the analyte concentration or level within the body, or in many other types of environments, there are certain problems associated with such a sensing system. One problem associated with single-mode fiberoptic interferometers is the extreme sensitivity to optical path length changes due to the transduction being accomplished by comparing the phase of two ultra-high frequency light beams. Various environmental effects can cause extraneous phase changes, including atmospheric pressure and temperature changes, optical connector movement, and undesired light source variations. These extraneous phase changes are collectively termed "phase noise".

Most phase noise can be minimized by exposing both arms 24 and 26 of the interferometer shown in FIG. 1 to the same environment. This can be accomplished by enveloping both arms 24 and 26, which preferably are of identical length, in a common sheath or covering, or by bonding the cladding of the two arms 24 and 26 together. Further, all physical modifications carried out with respect to the sensing arm 24 should also be carried out with respect to the reference arm 26. This includes any chemical milling or etching to expose the evanescent portion of the guided wave which should be done to both arms. Both milled or etched portions should be encased in material of similar steady-state refractive index, with similar diffusion coefficients for the analyte of interest, temperature, refractive index coefficients, and so on. Only the material on the sensing arm 24 should be treated to possess the analyte-specific activity required to enhance the change in refractive index in the presence of the analyte. This generally ensures that both arms will be exposed to similar environmental effects such as pressure and temperature changes.

This does not eliminate the phase noise problems in environments where fiber bending can be expected, for example, in hospital bedside monitoring devices where the optical fibers connect the optoelectronic base unit to the patient. Bending of the fiber within the arms of an interferometer can cause phase noise large enough to obscure analyte-induced optical path length changes. Despite bonding or common sheath enveloping of the two arms, the fibers are susceptible to bending noise whenever the fibers are deformed. Under almost any bending stress, the bonded fibers necessarily experience different strains since each fiber is located at a slightly different radial position with respect to the center of curvature of the bend. The different strains translate into different optical pathlength changes for each fiber under the same bending condition, leading to phase noise. It is impossible to effectively eliminate all mechanically-induced phase noise from a fiberoptic interferometer through mechanical conformation alone, even when the arms are coiled around one another or are formed as a co-extruded coaxial waveguide.

One method of compensating for environmentally-induced phase noise is to use a multiplicity of illumination sources, each multiplexed onto the interferometer in order to effect a ratiometric measurement. Demultiplexing the different waves after superposing them at coupler 20 relies upon various different attributes of the waves themselves. The three primary attributes of an electromagnetic wave are amplitude, frequency, and polarization angle, with all other attributes (e.g., wavelength, speed in a given medium, etc.) being derived in some sense from the three primary attributes. Accordingly, one or a combination of waves multiplexed onto the interferometer with one or more known attributes may be used in a ratiometric stabilization scheme, with demultiplexing effected via optical or electronic components designed to extract one particular wave based upon the defining attribute of that wave. Any of the defining attributes of an electromagnetic wave can be used to selectively multiplex and demultiplex the associated interferogram, subject to the availability of an optoelectronic scheme or device capable of discriminating between the various multiplexed waves on the basis of that attribute.

For example, two beams from two different sources each at a different frequency ("color", directly related to wavelength) can be brought together into the same interferometer via source fiber 16. Both beams undergo reflection at the terminal reflectors 98 and recombine at coupler 20, as before, where interference occurs at each frequency resulting in two overlaid, colinear interferograms, each at the wavelength of the respective illumination source. Both colinear interferograms are then passed to detector unit 36 via fiber 34. If a wavelength-selective filter, having a passband nominally located at the center wavelength of one of the two sources, is placed in front of detector unit 36, then the detector is rendered sensitive only to the interferogram derived from the associated source and not to the colinear interferogram.

The principle of superposition guarantees that mutual interference between the two colinear waves propagating in the interferometer cannot occur. Thus, placement of a wavelength-selective filter at the detector eliminates the contribution of the colinear interferogram altogether. If the filter passband is altered such that the second wavelength may propagate to the detector while the first is blocked, then the same situation pertains for the second interferogram.

Figure 6:
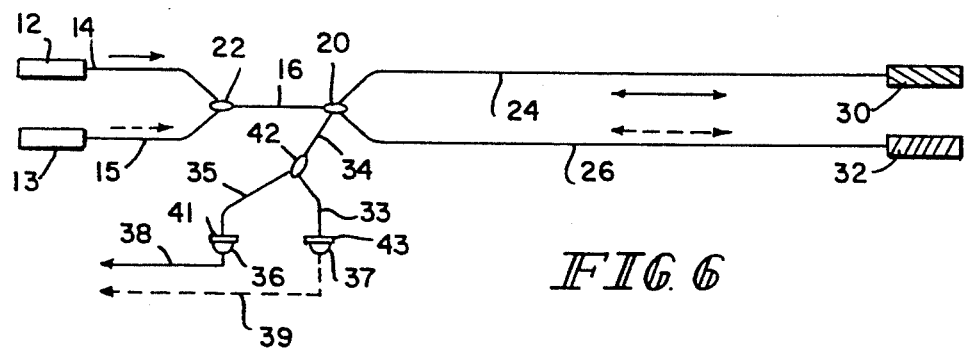
FIG. 6 is a diagrammatic view of a fiberoptic interferometric sensor according to the present invention employing multiple wavelengths.

A workable ratiometric system may be obtained by splitting fiber 34 as shown in FIG. 6 by coupler unit 42 into fibers 33 and 35 illuminating separate detector units 37 and 36, respectively. The detector units 36 and 37 incorporate a wavelength selective filter 41 and 43, respectively, designed to accept one wavelength but reject the other. Waves from two sources 12 and 13 are coupled to source fiber 16 by coupler unit 22 and by fibers 14 and 15, respectively. The waves from the two sources propagate through the system at different wavelengths, causing interferograms to be developed at those wavelengths. Each detector 36 and 37, receiving only one of the two interferograms through the filters 41 and 43, develops an electrical signal 38 and 39 indicative of the interferogram of one particular wavelength. Environmental phase noise affects both interferograms (ideally equally) whereas the sensor portion 30 can be constructed so as to differentially affect only one of the interferograms. The instantaneous ratio of both interference signals results in recovery of the differential analyte-induced signal while the common-mode environmental phase noise is suppressed. Nearly exact suppression of bending noise can be accomplished because the colinear waves now propagate in the same fiber core, guaranteeing identical bend radius of curvature for each of the two waves.

In practice, the phase sensitivity (i.e., change of phase for given optical pathlength change) is found to be linearly dependent on wavelength. The differential sensitivity of one wavelength relative to the other is controlled in part by the evanescent penetration depth of that particular wave. A deeply penetrating evanescent wave portion will give rise to a greater phase shift for a given refractive index change than will a shallow evanescent wave portion. As indicated previously, evanescent wave penetration depth can be controlled by a number of factors, including actual wavelength, external index mismatching, selective reflectance coatings, source power, etc.

Figure 7:
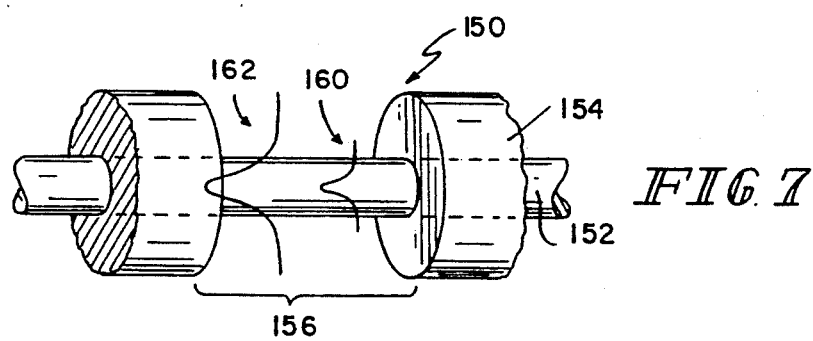
FIG. 7 is a much enlarged view of an etched optical fiber with two light waves diagrammatically shown in relation thereto.

FIG. 7 schematically illustrates an example of differential evanescent penetration depth in a fiber section 150. The fiber section 150 includes a core 152 and cladding 154 which has been etched in an etched portion 156. For illustrative purposes, a first wavefront 160 is illustrated which has a shallow evanescent penetration depth, and a second wavefront 162 is illustrated which has a relatively deep evanescent penetration depth. It will be understood that the second wave 162 would be utilized as the analyte wave, and would experience greater phase shift for a given refractive index change than would the shallow penetrating wave front 160.

A ratiometric system based upon two sources of different wavelengths will not consistently produce perfect cancellation of environmental phase noise because of the different sensitivities conferred by the different wavelengths themselves. It is therefore preferable to use sources of the same wavelength in order to eliminate this error and rely on another attribute for discrimination. One means for discriminating between waves of the same wavelength is their polarization. Two waves derived from the same source may be multiplexed onto and demultiplexed from one interferometer if the polarization angle of each wave differs by a measurable amount, and if that difference is maintained throughout the interferometric system.

It is known that the D-shaped fiber discussed previously is capable of propagating light aligned along both the major and minor axes of the core ellipse. If light emitted from a single laser source is split into two beams which are polarized at 90° with respect to one another, the D-shaped fiber will propagate the two polarizations along the two orthogonal axes without allowing cross-polarization interference to occur. Even under highly adverse bending conditions, the mixing of the light propagating along such a fiber at these two orthogonal polarizations is negligible. The separation tendency is so strong that the fiber itself will separate a single beam launched at a 45° orientation to either axis into equal, independently propagating, polarized components aligned with the major and minor axes. This eliminates the need for any separate device to create two orthogonally polarized input beams from the laser source. Two detector units may be used, as shown in FIG. 6, except that the filter elements 41 and 43 are now polarization sensitive rather than wavelength sensitive. Further, the wavelengths and wavelength-dependent environmental sensitivities of the two polarizations are identical.

As before, the sensor portion 30 must be constructed so as to differentially affect the two polarizations. This is easily accomplished as the evanescent penetration depth of the polarization aligned with the minor axis is greater than that of the other polarization where the two polarizations are of equal power. Variation in the relative power level of the two polarizations can be achieved by modifying the initial launch angle to be other than 45°. Thus the beam aligned with the minor axis is used to detect analyte-induced signals which are then measured by comparing the phase of the electrical signals 38 and 39 representing the interferograms of the two orthogonal polarizations. Since the wavelengths of the two polarizations are identical, the problem of different ratioing of wavelengths discussed previously is eliminated.

Figure 8:
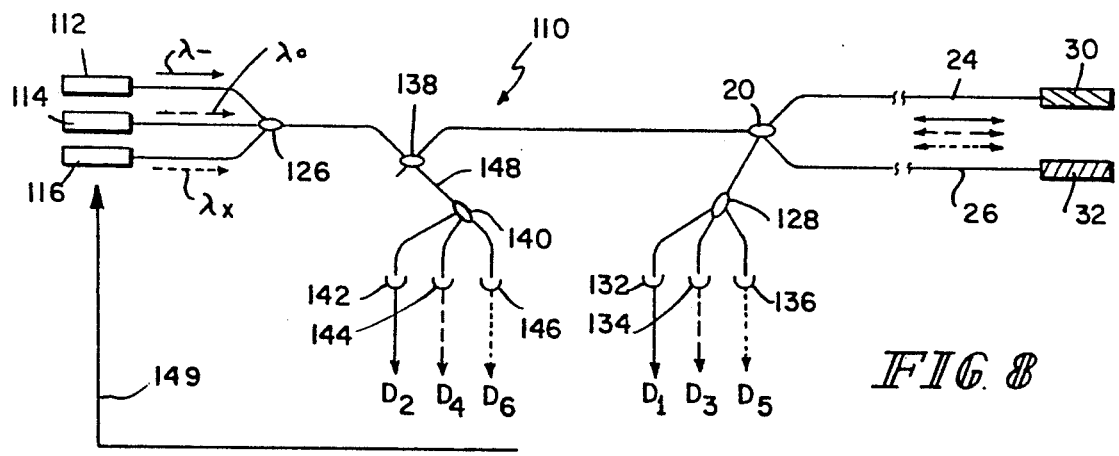
FIG. 8 is a diagrammatic view of a fiberoptic interferometric sensor according to the present invention employing multiple wavelengths.

Alternatively, three illumination sources may be used, each at a different wavelength selected to compensate for the differing phase sensitivities at each wavelength. FIG. 8 illustrates diagrammatically an example of an interferometric system 110 which utilizes three different wavelengths derived from three laser sources 112, 114, and 116. In this embodiment, the first laser source 112 produces light of a first wavelength $\lambda_-$, the second laser diode 114 produces light of a second wavelength $\lambda_o$, and the third laser diode 116 produces light of a third wavelength $\lambda_+$. The three wavelengths, $\lambda_-$, $\lambda_o$, and $\lambda_+$, are routed through a fiber optic coupler 126 and then through the coupler 20 into the sensing fiber 24 and the reference fiber 26. Although light at all three wavelengths $\lambda_-$, $\lambda_o$, and $\lambda_+$, is confined within the same single-mode fibers 24, 26, there is no interaction between the three different wavelengths themselves because of the lack of mutual coherence.

Light at each wavelength is subject to stress-induced phase shifting within the fibers 24, 26 due to bending and other environmental factors. A fiberoptic coupler 128 is provided which can provide for a demultiplexing of the three wavelengths $\lambda_-$, $\lambda_o$, and $\lambda_+$, with the separate wavelengths then being directed to a first detector unit 132, a second detector unit 134, and a third detector unit 136, respectively. Demultiplexing may occur at the coupler 128 which itself may be a wavelength-division demultiplexer, or at detectors 132, 134, and 136, each of which can contain appropriate bandpass filters as discussed previously. Outputs $D_1$, $D_3$, and $D_5$ are then provided by the first, second, and third detector units 132, 134, 136, respectively. A ratioing technique can then be utilized to compute a compensation factor for stress-induced disturbances within the fibers 24 and 26.

In order to effectively eliminate stress-induced errors including bending errors, all three wavelengths must be exposed to the noise-inducing path length changes such as by bending, but only one of the wavelengths will be exposed to the analyte-induced path length change. In general, attributes of the three wavelengths used in the method illustrated in FIG. 8 should be controlled such that the evanescent wave penetration depth of the central wavelength '$\lambda_o$' is greater than the amplitude of either of the other wavelengths, '$\lambda_+$' and '$\lambda_-$'. For instance, the polarization attribute of the central wavelength may be selected orthogonal to the other wavelengths, such that transmission of the central wavelength is constrained to the second major axis of the electrical polarization-preserving fiber core while the other two wavelengths propagate along the first axis. Also, to compute the compensation requires that all three wavelengths be equally spaced from each other, although no restriction is placed on the absolute value of the wavelength. A monitoring and autocorrection of the wavelengths can be achieved by positioning photodetectors 142, 144, and 146 at the end of fiber 148. The photodetectors are coupled to at least source 114, through feedback control loop 149, for ensuring that the proper wavelength relations of the three sources are maintained.

All of the various systems for dealing with phase noise assume that the source or sources emit light of known, stable character. However, each apparatus shown in FIGS. 1, 6, and 8 directs an interferogram back to the source as well as to the various detectors. The returning interferogram will enter the source or sources under arbitrary conditions of phase and amplitude depending upon external phase noise as well as analyte-induced phase modulation. In general, such arbitrary energy introduction into a laser source is known to destabilize the source causing mode-hopping, line broadening or narrowing, and large amplitude fluctuations. This is particularly true with narrowband sources, which are generally preferred in the present invention, where the total length of fiber travelled by the wave is much shorter than the longitudinal coherence length of the wave itself. In order to avoid this undesirable situation, some isolation means must be employed to protect the spectral integrity of the source.

Figure 9:
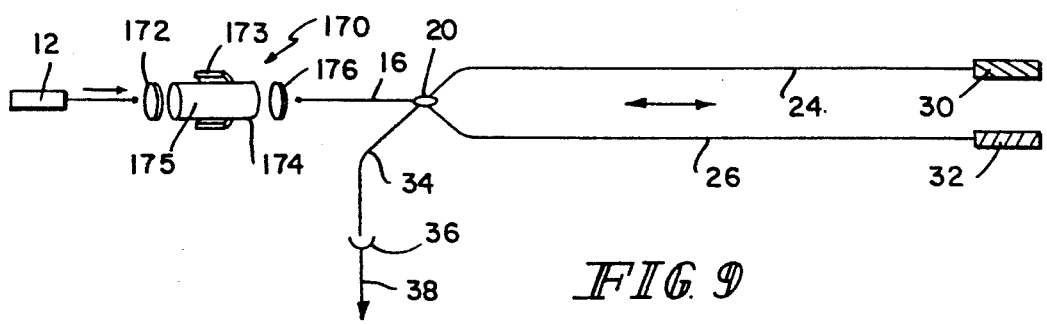
FIG. 9 is a diagrammatic view of a fiberoptic interferometric sensor according to the present invention employing apparatus for optical isolation of the source.

FIG. 9 illustrates an embodiment wherein the laser source 12 can be isolated from any returning power from the interferometric system of FIG. 1. In the preferred embodiment, the laser source 12 is a laser diode. To prevent the return of any portion of the reflected energy into the source, an isolator unit 170 consisting of a magneto-optic device 174 and polarizers 172 and 176 which together have the ability to transmit light with low loss in one direction, but effectively block light in the opposite direction. Extinction ratios of $-30$ dB to $-70$ dB are possible with single or cascaded isolator units of this type. Thus, the laser source generally functions as though no light were returning from the interferometric system.

Another method of isolating the laser diode source from returning radiation is to utilize a pulsed laser or provide some means by which the energy is gated between the laser 12 and the input fiber 16. In the embodiment shown in FIG. 10, the laser energy is gated between the laser 12 and the interferometer by a long length of single mode, polarization-preserving optical fiber 182 acting as a delay element 180. The laser 12 is pulsed or gated such that the laser returns to an "off" state before the laser energy has traversed the delay line and interferometer in both forward and reverse directions. The laser is therefore rendered insensitive to the returning radiation, even though the returning energy impinges upon the lasing cavity of the diode 12. For a pulse length of 0.1 microseconds, which is typical of conventional communication grade diodes, a delay line length of about 10 meters would suffice to prevent back-reflection from entering the active diode.

Figure 10:
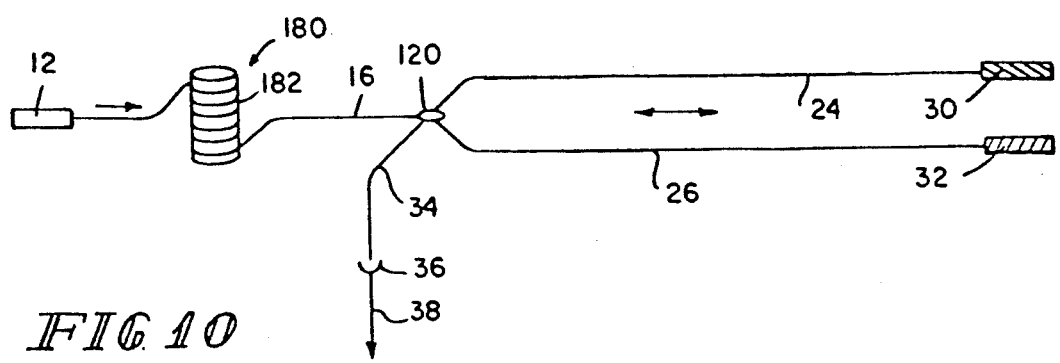
FIG. 10 is a diagrammatic view of a fiberoptic interferometric sensor according to the present invention employing another apparatus for optical isolation of the source.
Figure 11:
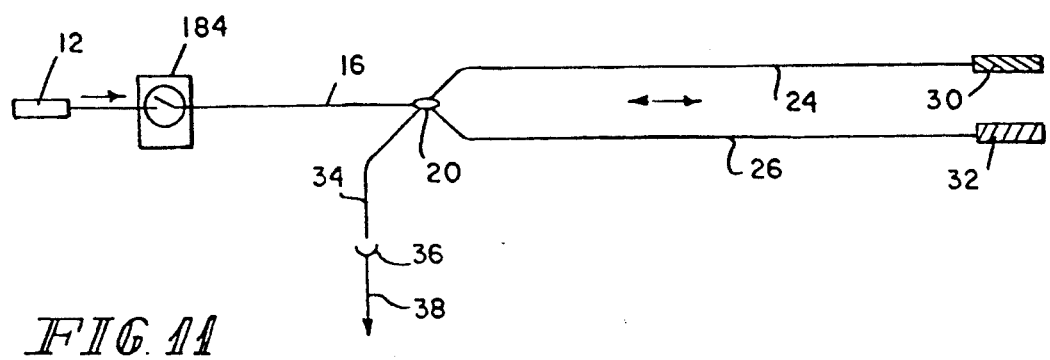
FIG. 11 is a diagrammatic view of a fiberoptic interferometric sensor according to the present invention employing yet another apparatus for optical isolation of the source.

FIG. 11 shows an alternative method using an ultrafast electro-optic modulator or switch 184. This type of modulator is generally composed of an implanted series of wave guides in lithium niobate or other electro-optic substrate. Picosecond switching times can be achieved by a modulator of this type which would allow the use of short delay line elements. An input fiber 16 having a length of a few centimeters could act as the delay element. Each of FIGS. 9-11 show a single frequency system but it will be appreciated that a multiple frequency system could be constructed using any of the principles illustrated. Various means for isolating the source other than those discussed in connection with FIGS. 9-11 may also be apparent to those versed in the art.

Another problem presented by sensor systems of the present invention relates to the inherent bidirectional information flow occurring in Michelson interferometers. The interferogram produced by a narrow-band coherent source such as a gas laser or laser diode is composed of a constant amplitude sinusoidal intensity variation as discussed previously. If this output is allowed to fall onto a single detector, only a scalar representation of the phase information may be derived, i.e. one value representing the relative phase difference between the sensing and reference waves. It is necessary to add a second detector to the system in order to derive a vector representation of the phase information, i.e., both relative phase difference and direction in which the phase is changing. This allows measurement of, or differentiation between, variables which may increase or decrease from a steady state value. The second detector, while exposed to the same interferogram as the first, must be positioned 90 degrees apart in phase from the first detector in order to properly derive the directional information. The 90 degree phase separation is generally termed a "quadrature" condition. However, so long as the two returning sensing and reference beams are confined in single mode fibers, the interference field generated exhibits a "recombinant spot" rather than "parallel fringe" appearance, and quadrature demodulation is not possible.

Figure 12A:
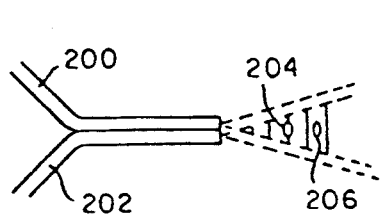
FIG. 12a is a diagrammatic view of a fiberoptic system for developing an interference field from which the direction of phase change can be determined.

FIG. 12a illustrates one method of developing an interferogram from which directional information can be obtained. The returning sensing and reference beams are directed parallel to each other by two fibers 200 and 202 separated generally by less than about 1 mm. The returning coherent beams emitted from fibers 200 and 202 combine in space to form a three dimensional interference field in which detectors 204 and 206 can be positioned to detect the direction of phase change. For a sinusoidal interferogram with distance between fringes of $\delta$ mm, a quadrature condition corresponds to a detector spacing in the fringe field of $n\delta/4$, where n is an integer multiple 1, 2, ... While the width and spacing of the interference fringes can be modified by varying the separation and tilt between the ends of the fibers, the free-space mixing zone detracts somewhat from the accuracy of the information when the phase shifts are small, due to environmental influences.

Figure 12B:
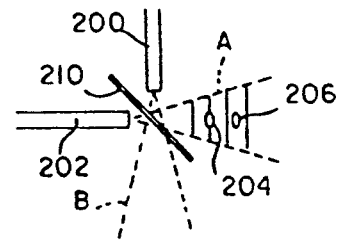
FIG. 12b is a diagrammatic view of a fiberoptic system for developing another interference field from which the direction of phase change can be determined.

Alternately, a three-dimensional interferogram can be generated by positioning the two fibers 200 and 202 so that the end-firing beams intersect at a partially reflecting mirror 210 as shown in FIG. 12b thereby developing two Michelson interference fields A and B. The detectors 204 and 206 can be positioned in either field to detect the direction of phase change. In both methods the two detectors are positioned with respect to each other and to the interference field so that they have a quadrature phase relation to one another as detailed above. While only two detectors are shown, additional detectors can be included in the fields to improve the resolution and accuracy of the measurements. It will also be appreciated that directional phase information can be obtained from the source as well as from the analyte.

Figure 13:
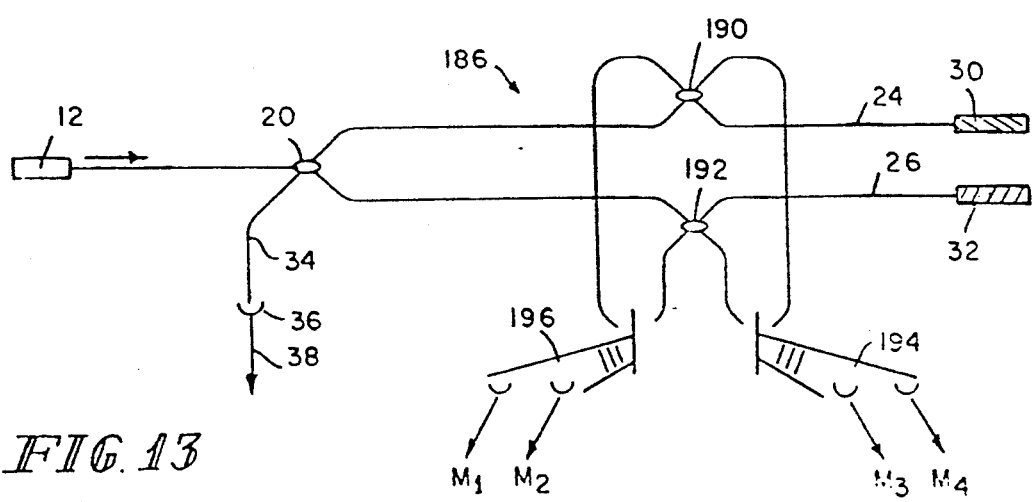
FIG. 13 is a diagrammatic view of a fiberoptic interferometric sensor according to the present invention employing both Mach-Zehnder and Michelson interferometric signals to evaluate both the source and the analyte.

FIG. 13 shows a hybrid Michelson/Mach-Zehnder interferometer 186 in which three-dimensional interferograms are employed to obtain the spectral signature of the source 12 as well as the return signal. In the illustrated apparatus, splitting of the signal from the source 12 occurs at coupler 20, while extraction of both the source and return signals occurs at couplers 190 and 192. In the case of a laser diode source 12, the relative phase between the sensing and reference waves propagating in the interferometer may be controlled by injection current and temperature modulation. However, such modulation affects the spectral signature of the source in a known and reproducible fashion. The spectral signature may be completely characterized by Fourier transformation of the quadrature-phase signals at outputs $M_3$ and $M_4$ taken from the Mach-Zehnder interference field 194. This technique is similar to that used in Fourier transform infrared spectroscopy (FTIR) since the autocorrelation and spectral density functions are a Fourier transform pair as described by the Wiener-Khintchine theorem. Continuous information regarding the source spectrum is important when on-line interferometric phase adjustment is necessary.

In the reverse direction, waves propagating back towards the primary coupler 20, after reflection at sensing and reference portions 30, 32, are partially extracted by couplers 190 and 192 to form a second interference field 196 from which quadrature-phase signals $M_1$ and $M_2$ can be obtained. These waves have made a double-pass through the sensing and reference portions 30, 32 and thus the signals $M_1$ and $M_2$ reflect this double-pass situation. The signals $M_1$ and $M_2$ can be used for high-resolution directional demodulation with ratiometric means added to the system for environmental phase noise suppression as previously discussed. The remainder of the energy propagating back towards the source along the sensing and reference arms is coherently mixed at coupler 20 and a primary "recombinant spot" Michelson interferogram formed at detector 36. This primary interferogram can be used in concert with the directional information described above to provide high resolution assessment of analyte-induced phase modulation.

The entire interferometric system 10, other than the sensing and reference arms 24 and 26, can be fabricated using implanted waveguide technology, with laser diode sources, detectors, couplers, and other elements integrated onto the same substrate. This electro-optic "chip" would then be connected to the sensing and reference fibers, with the only other connections being those electrical inputs and outputs required by the sources and detectors. Likewise, while only FIGS. 12 and 13 have illustrated a system in accordance with this invention using quadrature demodulation to determine the direction of sensed change in optical path length due to a change in refractive index, other systems can also use this same technique for obtaining this and other information. Additionally the quadrature demodulation described in connection with FIGS. 12 and 13 can be coupled with the triple wavelength phase noise reduction described in connection with FIG. 8 to isolate and accurately measure changes in analyte refractive index sensed by the evanescent portion of guided light travelling within the fiberoptic system.

Although the invention has been described in detail with reference to certain preferred embodiments and specific examples, variations and modifications exist within the scope and spirit of the invention as described and as defined in the following claims.

What is claimed is:

1. A method of detecting a change in a specimen comprising the steps of:
   a) providing a single-mode optical fiber with a segment permitting evanescent wave coupling to a contiguous medium;
   b) uniting the segment of the optical fiber with the specimen to permit evanescent wave interaction therewith;
   c) introducing light of known character into the optical fiber to traverse the segment, reflect from a reflector, and re-traverse the segment;
   d) constructing an interferogram with the light after it has re-traversed the segment; and
   e) observing the interferogram so as to detect any modulation in phase of the light due to a change in optical path length in the specimen.

2. The method of claim 1 further comprising the steps of:

introducing the light of known character into a second optical fiber; and optically superposing the light in the two optical fibers so as to develop the interferogram.

3. The method of claim 2 further comprising the steps of:

enveloping both the first and second optical fiber in a covering; and exposing both the first and second optical fiber to the same environmental effects to minimize phase noise.

4. The method of claim 1 further comprising the steps of:

introducing the light having two different values of a common attribute into the optical fiber;

observing the interferograms developed for both values of the common attribute so as to detect any modulation in phase of the light; and examining ratiometrically the observed modulations in phase to detect a change in optical path length in the specimen.

5. The method of claim 1 further comprising the steps of:

introducing the light having three different values of a common attribute into the optical fiber;

observing the interferograms developed for all values of the common attribute so as to detect any modulation in phase of the light;

calculating a compensation factor for any observed stress-induced disturbances in the optical fiber; and applying ratiometrically the calculated compensation factor to the observed modulations in phase to detect a change in optical path length in the specimen.

6. The method of claim 1 further comprising the steps of:

introducing the light of known character into the optical fiber so as to form two independently propagating, orthogonally polarized components;

permitting the evanescent wave of one of the components to interact with the specimen; and optically superposing the light from the two components with a reference two component beam so as to develop the interferogram.

7. The method of claim 1 further comprising the steps of:

submerging the segment of the optical fiber in a fluid specimen containing an analyte; and observing the interferogram so as to detect any change in phase due to a change in analyte concentration in the fluid specimen.

8. The method of claim 7 further comprising the step of:

introducing the segment of the optical fiber transdermally into a specimen fluid for intervivos detection of a change in analyte concentration.

9. A method of suppressing noise in a fiberoptic interferometric system for detecting a change in concentration of an analyte in a fluid medium comprising the steps of:

a) supplying the system with light having a plurality of wavelengths, the wavelengths being spaced from each other sufficiently to permit optical separation of one wavelength from another, b) allowing an evanescent portion of only one wavelength of light to interact with the medium while all wavelengths are exposed to noise-induced pathlength changes in the system;

c) generating an interferogram for each wavelength; and d) comparing the difference in movement of the interferograms to detect the analyte-induced pathlength change.

10. The method of claim 9 wherein the wavelengths selected consist essentially of a central wavelength $\lambda_o$ and two wavelengths, $\lambda_+$ and $\lambda_-$, spaced equally on either side of the central wavelength.

11. The method of claim 10 wherein the central wavelength $\lambda_o$ is selected such that the energy of its evanescent portion in the surrounding medium is greater than the other wavelengths $\lambda_-$ and $\lambda_+$.

12. The method of claim 9 wherein the amplitudes of the selected wavelengths are such that the amplitude of the central wavelength '$\lambda_o$' is greater than the amplitude of either of the other wavelengths, '$\lambda_+$' and '$\lambda_-$'.

13. Apparatus for detecting a change in a medium comprising:

a) a first and a second optical fiber, at least the first optical fiber having a portion which allows an evanescent portion of a light wave traveling within the fiber to interact with the medium surrounding said portion of the first fiber b) means for introducing a light of known character into the optical fibers;

c) means at an end portion of the optical fibers for reflecting the light from the end portion back toward the introducing means;

d) means for optically superposing the reflected light in the two optical fibers so as to develop an interference zone; and e) means for observing the zone so as to detect any change in phase due to a change in the fluid medium.

14. The apparatus of claim 13 wherein at least the first optical fiber consists essentially of a single mode fiber.

15. The apparatus of claim 14 wherein the single mode fiber comprises a polarization preserving fiber.

16. The apparatus of claim 15 wherein the polarization preserving fiber comprises an elliptical core and a rotationally asymmetric cladding.

17. The apparatus of claim 16 wherein the cladding comprises an outer wall having a planar segment joined to a cylindrical segment to form a generally D-shaped cross-section, the elliptic core being situated closest to the planar segment of the outer wall.

18. The apparatus of claim 13 wherein said portion of the first fiber is of reduced cross-sectional dimension.

19. A sensing device for determining the concentration of an analyte in a fluid medium, the sensing device comprising, a) a light source that produces at least one distinct wavelength light signal, b) a first single mode fiber element coupled to the light source for receiving and transmitting the light signal from the light source, c) a sensor portion disposed along the first fiber element for interacting with an analyte to modulate the phase of the light signal, d) a second single mode fiber element coupled to the light source for guiding the light signal from the light source, e) means at an end portion of the optical fiber elements for reflecting the light from the end portion back toward the light source; and f) means for comparing the phase of the light signal carried by the first fiber element after interaction with the analyte with the phase of the light signal carried by the second fiber element to determine the concentration of the analyte.

20. The sensing device of claim 19 wherein the light source comprises a source of light signals having at least two distinct attributes which are transmitted through both the first fiber element and the second fiber element.

21. The sensing device of claim 19 further comprising means for coupling the light source to the first single mode fiber so that the light is split into two beams which are polarized at 90° with respect to one another.

22. The sensing device of claim 21 wherein the sensor portion of the first fiber element comprises means for permitting only a single polarized beam to interact with the analyte to modulate the phase of the light signal.

23. The sensing device of claim 21 wherein the coupling means comprises means for modifying the initial launch angle of the light into the first single mode fiber to modify the relative power level of the two polarizations.

24. An optical fiber interferometric system comprising:
a) a single-mode, polarization-preserving fiber having an asymmetric cladding, a selected portion of the cladding having been removed to expose at least one side of the core;
b) means enveloping said selected portion in a material having a known index of refraction;
c) a second single-mode, polarization-preserving fiber and means for introducing a light of known character into the optical fibers;
d) means at an end portion of the optical fibers for reflecting the light from the end portion back toward the light introducing means;
e) means for optically superposing the reflected light in the two optical fibers so as to develop an interference zone; and
f) means for observing the zone to detect any change in index of refraction of said material.

25. The optical fiber interferometric system of claim 24 wherein the material forming the enveloping means around said selected portion is selected so that a physical change in the environment of the enveloping means causes a change in the index of refraction of said material.

26. The optical fiber interferometric system of claim 25 wherein the wavelength of the light is selected to lie in an anomalous dispersion spectral region of the material forming the enveloping means.

27. The optical fiber interferometric system of claim 25 wherein the wavelength of the light is selected to correspond to the maximum rate of change of chemical absorbance with wavelength for the material forming the enveloping means.

28. A sensing device for determining the concentration of an analyte in a fluid medium, the device comprising,
a) a first optical fiber including a core and a cladding which surrounds the core, with a section of the cladding removed to expose a portion of the core,
b) a second optical fiber,
c) means for introducing a light of known characteristics into the first and second optical fibers such that the light in the first optical fiber is influenced by the concentration of the analyte, and
d) means at an end portion of the optical fibers for reflecting the light from the end portion back toward the light introducing means;
e) means for comparing the phase of the reflected light in the first optical fiber after it has been influenced by the concentration of the analyte with the phase of the light in the second optical fiber such that the concentration of the analyte can be determined.

29. The device of claim 28 further comprising means for blocking the reflected light from entering the introducing means.

30. The device of claim 29 wherein the blocking means comprises a magnetic-optic isolator unit which magnetically orients a polarization characteristic of the light such that the reflected light is prevented from entering the introducing means.

31. The device of claim 29 wherein the introducing means comprises a laserdiode.

32. The device of claim 31 wherein the introducing means further comprises a fiber optic coupler unit which couples the laser diode to the first optical fiber.

33. The device of claim 31 wherein the blocking means comprises means for delaying the light after exiting the laser diode and before entering the first optical fiber.

34. The device of claim 31 wherein the blocking control the light emitted by the laser diode.

35. An optical fiber interferometric system comprising:
a) a pair of single-mode, polarization-preserving fibers, a selected portion of the cladding of one of the fibers having been removed to allow an evanescent portion of a light wave traveling within the fiber to interact with any medium surrounding the fiber, the two optical fibers have distal and proximal ends;
b) a light source for producing a light of known character and a fiberoptic coupler joining the light source to the proximal ends of the two optical fibers;
c) means at the distal ends of the optical fibers for reflecting the light from the distal ends back toward the light source;
d) means optically superposing the reflected light in the two optical fibers for developing an interference zone; and
e) means for observing the interference zone to detect any change in index of refraction of said medium surrounding said selected portion.

36. The apparatus of claim 35 wherein the light source comprises means for emitting a plurality of selected wavelengths.

37. The apparatus of claim 36 wherein the means for observing the light comprises means for demultiplexing the light into the various selected wavelengths.

38. The apparatus of claim 37 wherein the wavelengths selected consist essentially of a central wavelength $\lambda_o$ and two wavelengths, $\lambda_+$ and $\lambda_-$, spaced equally on either side of the wavelength.

39. The apparatus of claim 38 wherein the central wavelength $\lambda_o$ is selected such that the energy of its evanescent portion in the surrounding medium is greater than the other wavelengths $\lambda_-$ and $\lambda_+$.

40. The apparatus of claim 38 wherein a measurable attribute of each of the selected wavelengths is such that the attribute of the central wavelength '$\lambda_o$' is greater than the attribute of either of the other wavelengths, '$\lambda_+$' and '$\lambda_-$'.

41. An optical fiber interferometric system comprising:

a) a pair of single-mode, polarization-preserving fibers, the cladding of a selected portion of one of the fibers having been removed to allow an evanescent portion of a light wave traveling within the fiber to interact with any medium surrounding the selected portion of the fiber, the pair of optical fibers have distal and proximal ends;
b) a light source for producing a light of known character;
c) a first fiberoptic coupler joining the light source to the proximal ends of the pair of optical fibers for introducing the source signal to the pair of fibers;
d) means at the distal ends of the optical fibers for reflecting the light from the distal ends back toward the light source; and
e) means for observing the return signal in the first fiberoptic coupler to detect any change in index of refraction of said medium surrounding said selected portion.

42. The apparatus of claim 41 further comprising a second fiberoptic coupler and an optical fiber connecting the light source to the first fiberoptic coupler.

43. The apparatus of claim 42 further comprising means connected to the second fiberoptic coupler for monitoring the emission characteristics of the light source.

44. The apparatus of claim 42 further comprising means connected to the second fiberoptic coupler for extracting a quadrature signal for detecting the direction of change in index of refraction of said medium surrounding said selected portion.

45. The apparatus of claim 41 wherein the light source further comprises isolation means for isolating the source from light reflected from the distal ends of the pair of fibers.

46. The apparatus of claim 41 further comprising an additional fiberoptic coupler situated in each of said pair of fibers for dividing the source signal and the return signal 47. The apparatus of claim 46 further comprising means coupled to both of said additional fiberoptic couplers for developing an interferogram of the source signal.

48. The apparatus of claim 47 further comprising means coupled to both of said additional fiberoptic couplers for developing an interferogram of the return signal.

* * * * *